United States Patent
Hartle et al.

(10) Patent No.: US 7,520,089 B2
(45) Date of Patent: Apr. 21, 2009

(54) METHOD TO IMPROVE MANUFACTURED SEED GERMINATION

(75) Inventors: Jeffrey E. Hartle, Tacoma, WA (US); William C. Carlson, Olympia, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 33 days.

(21) Appl. No.: 10/982,627

(22) Filed: Nov. 4, 2004

(65) Prior Publication Data

US 2005/0150161 A1 Jul. 14, 2005

Related U.S. Application Data

(60) Provisional application No. 60/525,443, filed on Nov. 25, 2003.

(51) Int. Cl.
*A01H 4/00* (2006.01)

(52) U.S. Cl. ............................ 47/58.1 SE; 435/422

(58) Field of Classification Search .................. 47/58.4, 47/57.6; 435/422
See application file for complete search history.

(56) References Cited

U.S. PATENT DOCUMENTS

| | | | |
|---|---|---|---|
| 4,217,730 A | 8/1980 | Abo El-Nil | |
| 4,801,545 A | 1/1989 | Stuart et al. | |
| 4,957,866 A | 9/1990 | Gupta et al. | |
| 5,034,326 A * | 7/1991 | Pullman et al. | 435/422 |
| 5,036,007 A | 7/1991 | Gupta et al. | |
| 5,041,382 A | 8/1991 | Gupta et al. | |
| 5,183,757 A | 2/1993 | Roberts | |
| 5,187,092 A | 2/1993 | Uddin | |
| 5,236,841 A | 8/1993 | Gupta et al. | |
| 5,238,835 A | 8/1993 | McKersie et al. | |
| 5,294,549 A | 3/1994 | Pullman et al. | |
| 5,413,930 A * | 5/1995 | Becwar et al. | 435/422 |
| 5,464,769 A | 11/1995 | Attree et al. | |
| 5,482,857 A | 1/1996 | Gupta et al. | |
| 5,491,090 A | 2/1996 | Handley, III et al. | |
| 5,501,972 A | 3/1996 | Westcott | |
| 5,506,136 A | 4/1996 | Becwar et al. | |
| 5,523,230 A | 6/1996 | Smith | |
| 5,534,433 A | 7/1996 | Coke | |
| 5,534,434 A | 7/1996 | Coke | |
| 5,563,061 A * | 10/1996 | Gupta | 435/422 |
| 5,564,224 A | 10/1996 | Carlson et al. | |
| 5,565,355 A * | 10/1996 | Smith | 435/422 |
| 5,587,312 A | 12/1996 | van Holst et al. | |
| 5,610,051 A | 3/1997 | Becwar et al. | |
| 5,677,185 A | 10/1997 | Handley, III | |
| 5,701,699 A * | 12/1997 | Carlson et al. | 47/57.6 |
| 5,731,191 A | 3/1998 | Rutter et al. | |
| 5,731,203 A | 3/1998 | Handley, III | |
| 5,731,204 A | 3/1998 | Rutter et al. | |
| 5,821,126 A * | 10/1998 | Durzan et al. | 435/422 |
| 5,840,581 A | 11/1998 | Carraway et al. | |
| 5,850,032 A | 12/1998 | Wann | |
| 5,856,191 A * | 1/1999 | Handley, III | 435/422 |
| 5,985,667 A | 11/1999 | Attree et al. | |
| 6,022,744 A | 2/2000 | Tetteroo et al. | |
| 6,117,678 A | 9/2000 | Carpenter et al. | |
| 6,134,830 A * | 10/2000 | Welty | 47/58.1 R |
| 6,150,167 A | 11/2000 | Carpenter et al. | |
| 6,180,405 B1 | 1/2001 | Aitken-Christie et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,417,001 B2 | 7/2002 | Aitken-Christie et al. | |
| 6,444,467 B1 * | 9/2002 | Fan et al. | 435/430.1 |
| 6,492,174 B1 | 12/2002 | Pullman et al. | |
| 6,689,609 B1 * | 2/2004 | Fan et al. | 435/422 |
| 2002/0012994 A1 | 1/2002 | Aitken-Christie et al. | |
| 2002/0092037 A1 | 7/2002 | Connett-Porceddu et al. | |
| 2002/0100083 A1 | 7/2002 | Connett-Porceddu et al. | |
| 2003/0167684 A1 * | 9/2003 | Carlson et al. | 47/57.6 |
| 2005/0150161 A1 * | 7/2005 | Hartle et al. | 47/58.1 SE |
| 2007/0000169 A1 * | 1/2007 | Hartle | 47/58.1 SE |

FOREIGN PATENT DOCUMENTS

| | | |
|---|---|---|
| EP | 0 300 730 B1 | 1/1989 |
| EP | 0 618 766 B1 | 10/1994 |
| EP | 0 934 691 A2 | 8/1999 |
| WO | WO 95/33822 A1 | 12/1995 |
| WO | WO 98/48279 A1 | 10/1998 |
| WO | WO 99/46977 | 9/1999 |
| WO | WO 01/20972 A1 | 9/2000 |

OTHER PUBLICATIONS

WO 99/26470: Carlson and Hartle; 1999.*

Attree, S.M. et al., "Somatic Embryo Maturation, Germination, and Soil Establishment of Plants of Black and White Spruce (*Picea mariana* and *Picea glauca*)," Can. J. Bot. 68:2583-2589, 1990.

(Continued)

Primary Examiner—Francis T Palo
(74) Attorney, Agent, or Firm—Christsen O'Connor Johnson Kindness

(57) ABSTRACT

The invention provides methods for improving the germination of manufactured seeds. The methods comprise the steps of: (a) culturing a plant embryo in a germination medium; and (b) assembling the cultured plant embryo into a manufactured seed. The methods of the invention are applicable to zygotic and somatic plant embryos.

17 Claims, No Drawings

OTHER PUBLICATIONS

Attree, S.M., et al., "Initiation of Embryogenic Callus and Suspension Cultures, and Improved Embryo Regeneration of Protoplasts, of White Spruce (*Picea glauca*)," *Can. J. Bot. 67*:1790-1795, 1989.

Attree, S.M., et al., "Plantlet Regeneration From Embryogenic Protoplasts of White Spruce (*Picea glauca*)," *Bio/Technology 7*:1060-1062, 1989.

Boulay, M.P., et al., "Development of Somatic Embryos From Cell Suspension Cultures of Norway Spruce (Picea abies Karst.)," Plant Cell Reports 7:134-137, 1988.

Cornu, D. and C. Geoffrion, "Aspects of Somatic Embryogenesis in Larch Trees," *Bull. Soc. Bot. Fr.*, 137 Actual. Bot. (3/4):25-34, 1990 [translation].

Garin E et al, "Effects of sugars, amino acids, and culture technique on maturation of somatic embryos of Pinus strobes on medium with two gellan gum concentrations," *Plant Cell Tiss & Org Cult* (62) 27-27, 2000.

Gupta, P.K., et al., "Scale-Up Somatic Embryogenesis of Conifers For Reforestation," Proceedings of the 3rd Canadian Workshop on Plant Tissue Culture and Genetic Engineering, University of Guelph, Symposium 1: Somatic Embryogenesis and Synthetic Seeds, Abstract, Jun. 1992.

Hakman, I. and L.C. Fowke, "An Embryogenic Cell Suspension Culture of *Picea glauca* (White Spruce)," *Plant Cell Reports 6*:20-22, 1987.

Jain, S.M., et al., Forestry Sciences: Somatic Embryogenesis in Woody Plants, vol. 3, Gymnosperms, Kluwer Academic Publishers, Netherlands, 1995.

Keinonen-Mettälä, K., et al., "Somatic Embryogenesis of *Pinus sylvestris*," Scand. J. For. Res. 11:242-250, 1996.

Klimaszewska K et al, "Maturation of somatic embryos of pinus strobes is promoted by a high concentration of gellan gum," *Physiologica Plantarum* (100) 949-957, 1997.

Krogstrup, P. "Somatic Embryogenesis in Sitka Spruce (*Picea sitchensis* (Bong.) Carr.)," *Plant Cell Reports 7*:594-597, 1988.

Lelu Ma et al, "Somatic embryogenesis and plantlet development in *Pinus sylvestris* and *Pinus pinaster* on median with and without growth regulators," *Phys Plantarum, Munksgaard Intl* (105) 719-718, 1999.

Lelu, M.A. et al., "Effect of Maturation Duration on Desiccation Tolerance in Hybrid Larch (*Larix X leptoeuropaea dengler*) Somatic Embryos," *In Vitro Cell. Dev. Biol. 31*15-20, 1995.

Lu, C.-Y. and T.A. Thorpe, "Somatic Embryogenesis and Plantlet Regeneration in Cultured Immature Embryos of *Picea glauca*," *J. Plant Physiol. 128*:297-302, 1987.

Mathur, G. et al., "Studies on Somatic Embryogenesis From Immature Zygotic Embryos of CHIR Pine (Pinus roxburghii Sarg.)," Current Science 79(7):999-1004, 2000.

Norgaard, J.V., and P. Krogstrup, "Cytokinin Induced Somatic Embryogenesis From Immature Embryos of *Abies nordmanniana* Lk.," *Plant Cell Reports 9*:509-513, 1991.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant 37*:29-34.

Roberts, D.R., "Abscisic Acid and Mannitol Promote Early Development, Maturation and Storage Protein Accumulation in Somatic Embryos of Interior Spruce," *Physiologia Plantarum 83*:247-254, 1991.

Roberts, D.R et al., "Interaction Between Maturation and High Relative Humidity Treatments and Their Effects on Germination of Sitka Spruce Somatic Embryos," *J. Plant Physiol. 138*:1-6, 1991.

Roberts, D.R., et al., "Synchronous and High Frequency Germination of Interior Spruce Somatic Embryos Following Partial Drying at High Relative Humidity," *Can. J. Bot. 68*:1086-1090, 1989.

Taber RP et al., "Kinetics of Douglas-fir (*Pseudotsungo menziesii*) somatic embryo development," *Can J Bot* (76): 838-871, 1998.

Thompson, R.G. and P. von Aderkas, "Somatic Embryogenesis and Plant Regeneration From Mature Embryos of Western Larch," *Plant Cell Reports 11*:379-386, 1992.

Timmis, R., "Bioprocessing for Tree Production in the Forest Industry: Conifer Somatic Embryogenesis," Biotechnol. Prog. 14(1):156-166, 1998.

Von Aderkas, P., et al., "Charcoal Affects Early Development and Hormonal Concentrations of Somatic Embryos of Hybrid Larch," Tree Physiology 22:431-434, 2002.

Von Arnold, S. and I. Hakman, "Regulation of Somatic Embryo Development in *Picea abies* by Abscisic Acid (ABA)," *J. Plant Physiol. 132*:164-169, 1988.

Von Arnold, S. and T. Eriksson, "A Revised Medium for Growth of Pea Mesophyll Protoplasts," *Physiol. Plant 39*:257-260, 1977.

Webb, D.T., et al., "Factors Influencing the Induction of Embryogenic and Caulogenic Callus From Embros of *Picea glauca* and *P. engelmanii,*" *Can. J. For. Res. 19*:1303-1308, 1989.

\* cited by examiner

METHOD TO IMPROVE MANUFACTURED SEED GERMINATION

CROSS REFERENCE TO RELATED APPLICATION

The present application claims the benefit of U.S. Provisional Application No. 60/525,443, filed Nov. 25, 2003.

FIELD OF THE INVENTION

The invention relates to improving the germination of manufactured seeds containing plant embryos.

BACKGROUND OF THE INVENTION

It is often desirable to plant large numbers of genetically identical plants that have been selected to have advantageous properties, but in many cases it is not feasible to produce such plants using standard breeding techniques. In vitro culture of somatic or zygotic plant embryos can be used to produce large numbers of genetically identical embryos that have the capacity to develop into normal plants. However, the resulting embryos lack the protective and nutritive structures found in natural botanic seeds that shelter the plant embryo inside the seed from the harsh soil environment and nurture the embryo during the critical stages of sowing and germination. Attempts have been made to provide such protective and nutritive structures by using manufactured seeds, but so far germination from manufactured seeds is less successful than from natural seeds.

There is a need for an improved manufactured seed that more closely mimics the function of natural seeds to provide a large number of normal germinants. The present invention addresses this and other needs.

SUMMARY OF THE INVENTION

The invention provides methods for improving the germination of manufactured seeds. The methods comprise the steps of: (a) culturing a plant embryo in a germination medium; and (b) assembling the cultured plant embryo into a manufactured seed. The methods of the invention are applicable to zygotic or somatic embryos from any plant species, including conifers. For example, the plant embryo may be a Douglas-fir post-development somatic embryo or a loblolly pine post-development somatic embryo. In some embodiments, the methods comprise the steps of: (a) culturing plant tissue in an initiation medium to form embryogenic cells; (b) culturing the embryogenic cells of step (a) in a maintenance media to form multiplied embryogenic cells; (c) culturing the multiplied embryogenic cells of step (b) in a development medium to form somatic embryos; (d) culturing the somatic embryos of step (c) under conditions that promote embryo maturity to form post-development somatic embryos; (e) culturing the post-development somatic embryos of step (d) in a germination medium to form cultured post-development somatic embryos; and (f) assembling the cultured post-development somatic embryos of step (e) into manufactured seeds.

Suitable germination media typically comprise a carbon source, such as a monosaccharide or a polysaccharide. For example, the carbon source may be at least one of sucrose, glucose, fructose, and maltose. The germination medium may also comprise other plant nutrients, such as amino acids, polyamines, and minerals. The germination medium may also comprise an adsorbent composition. Suitable adsorbent compositions include, but are not limited to, charcoal, polyvinyl polypyrolidone, and silica gels.

In some embodiments, the germination medium comprises at least 8 components selected from the group consisting of: charcoal, a carbon source, urea, $KNO_3$, $NH_4NO_3$, $CuCl_2$, $CuSO_4$, KI, $KH_2PO_4$, $CaCl_2$, $MgSO_4$, $Na_2EDTA$, $FeSO_4$, ferric citrate, $MnSO_4$, $MnCl_2$, $H_3BO_3$, $ZnSO_4$, $CoCl_2$, $Na_2MoO_4$, $(NH_4)_2MoO_4$, thiamine, riboflavin, pyridoxine, HCl, Ca-pantothenate, nicotinic acid, biotin, folic acid, and myo-inositol. Additionally, the germination medium may comprises at least one component selected from the group consisting of: amino acids, polyamines, oxygen-carrying compounds, and a smoke suspension.

The plant embryo may be cultured in a germination medium for between about 8 hours and about 30 hours, such as between about 12 hours and about 24 hours, such as between about 16 hours and about 22 hours.

DETAILED DESCRIPTION OF THE PREFERRED EMBODIMENT

Unless specifically defined herein, all terms used herein have the same meaning as they would to one skilled in the art of the present invention.

Unless stated otherwise, all concentration values that are expressed as percentages are weight per volume percentages.

In a first aspect, the invention provides methods for improving the germination of manufactured seeds. The methods of the first aspect comprise the following steps: (a) culturing a plant somatic embryo in a germination medium; and (b) assembling the cultured plant somatic embryo into a manufactured seed.

The first step of the methods comprises culturing a plant embryo in a germination medium. As used herein, "a plant embryo" refers to either a zygotic embryo or a somatic embryo from a plant. A zygotic plant embryo is an embryo found inside a botanic seed produced by sexual reproduction. An exemplary method for producing plant zygotic embryos suitable for use in the methods of the invention is described in EXAMPLE 2, below.

A somatic embryo is an embryo produced by culturing totipotent plant cells such as meristematic tissue under laboratory conditions in which the cells comprising the tissue are separated from one another and urged to develop into minute complete embryos. Alternatively, somatic embryos can be produced by inducing "cleavage polyembryogeny" of zygotic embryos. Methods for producing plant somatic embryos suitable for use in the methods of the invention are standard in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). For example, plant tissue may be cultured in an initiation medium that includes hormones to initiate the formation of embryogenic cells, such as embryonic suspensor masses that are capable of developing into somatic embryos. The embryogenic cells may then be further cultured in a maintenance medium that promotes establishment and multiplication of the embryogenic cells. Subsequently, the multiplied embryogenic cells may be cultured in a development medium that promotes the development of somatic embryos, which may further be subjected to post-development treatments such as cold treatments.

The somatic embryos used in the methods of the invention are generally post-development embryos. Post-development embryos have completed the development stage of the somatic embryogenesis process and have undergone a cold treatment or other post-development media treatments that promote embryo maturity. The use of cold-treated somatic embryos in the methods of the invention is described in EXAMPLES 2 and 3.

Typically, the plant embryos used in the invention have a shoot end and a root end. In some species of plants, the shoot end includes one or more cotyledons (leaf-like structures) at some stage of development. Plant embryos suitable for use in the methods of the invention may be from any plant species, such as dicotyledonous or monocotyledonous plants, gymnosperms, etc.

The term "germination medium" refers to a medium comprising a source of nutrients, such as vitamins, minerals, carbon and energy sources, and other beneficial compounds that facilitate the biochemical and physiological processes occurring during germination. The germination medium typically comprises one or more carbon sources, vitamins, and minerals. Representative carbon sources include monosaccharides, disaccharides, and/or starches. For example, the germination medium may contain one or more carbohydrates such as sucrose, fructose, maltose, galactose, mannose, lactose, and the like. In some embodiments, the carbon source is sucrose. The total concentration of the carbon source in the germination medium may be from about 5 g/l to about 80 g/l, such as from about 20 g/l to about 60 g/l or from about 30 g/l to about 50 g/l.

The germination medium may also may also comprise amino acids, an adsorbent composition, and a smoke suspension. Suitable amino acids may include amino acids commonly found incorporated into proteins as well as amino acids not commonly found incorporated into proteins, such as argininosuccinate, citrulline, canavanine, ornithine, and D-steroisomers. A suitable concentration of protein amino acids in the germination medium is 0 mM to about 8 mM, such as about 0.01 mM to about 4 mM. A suitable concentration of non-protein amino acids in the germination medium is 0 mM to about 8 mM, such as about 1 mM to about 5 mM.

Suitable adsorbent compositions include, but are not limited to, charcoal, polyvinyl polypyrolidone, and silica gels. A suitable concentration of an adsorbent composition is 0 g/l to about 5 g/l, such as about 2 g/l to about 3 g/l.

A suitable smoke suspension contains one or more compounds generated through the process of burning organic matter, such as wood or other cellulosic material. Solutions containing these by-products of burning organic matter may be generated by burning organic matter, washing the charred material with water, and collecting the water. Solutions may also be obtained by heating the organic matter and condensing and diluting volatile substances released from such heating. Certain types of smoke suspensions may be purchased from commercial suppliers, for example, Wright's Concentrated Hickory Seasoning Liquid Smoke (B&G foods, Inc. Roseland, N.J. 07068). Smoke suspension may be incorporated into the nutritive medium in any of various forms. For instance, smoke suspension may be incorporated as an aerosol, a powder, or as activated clay. An exemplary concentration of Wright's Concentrated Hickory Seasoning Liquid Smoke liquid smoke suspension, if present, is between 0.0001 ml and 1 ml of smoke suspension per liter of medium. The germination medium may also include one or more compounds involved in nitrogen metabolism, such as urea or polyamines.

The germination medium may also contain hormones. Suitable hormones include, but are not limited to, abscisic acid, cytokinins, auxins, and gibberellins. Abscisic acid is a sesquiterpenoid plant hormone that is implicated in a variety of plant physiological processes (see, e.g., Milborrow (2001) *J. Exp. Botany* 52: 1145-1164; Leung & Giraudat (1998) *Ann. Rev. Plant Physiol. Plant Mol. Biol.* 49: 199-123). Auxins are plant growth hormones that promote cell division and growth. Exemplary auxins for use in the germination medium include, but are not limited to, 2,4-dichlorophenoxyacetic acid, indole-3-acetic acid, indole-3-butyric acid, naphthalene acetic acid, and chlorogenic acid. Cytokinins are plant growth hormones that affect the organization of dividing cells. Exemplary cytokinins for use in the germination medium include, but are not limited to, e.g., 6-benzylaminopurine, 6-furfurylaminopurine, dihydrozeatin, zeatin, kinetin, and zeatin riboside. Gibberellins are a class of diterpenoid plant hormones (see, e.g., Krishnamoorthy (1975) Gibberellins and Plant Growth, John Wiley & Sons). Representative examples of gibberellins useful in the practice of the present invention include gibberellic acid, gibberellin 3, gibberellin 4 and gibberellin 7. An example of a useful mixture of gibberellins is a mixture of gibberellin 4 and gibberellin 7 (referred to as gibberellin 4/7), such as the gibberellin 4/7 sold by Abbott Laboratories, Chicago, Illinois.

When abscisic acid is present in the germination medium, it is typically used at a concentration in the range of from about 1 mg/L to about 200 mg/L. When present in the germination medium, the concentration of gibberellin(s) is typically between about 0.1 mg/L and about 500 mg/L. Auxins may be used, for example, at a concentration of from 0.1 mg/L to 200 mg/L. Cytokinins may be used, for example, at a concentration of from 0.1 mg/L to 100 mg/L.

The composition of the nutrients in the germination medium may be similar or identical to the composition of the nutrients in the nutritive medium typically provided within a manufactured seed and described below. Representative germination media useful in the methods of the invention are NM1 and NM2, the composition of which are provided in Table 1.

According to the first step of the invention, a plant embryo is cultured in the germination medium. The plant embryo, such as a conifer somatic embryo, is typically cultured in the germination medium for a period between about 8 hours and about 30 hours, such as for a period between about 12 hours and about 24 hours, such as between about 16 hours and 22 hours. For example, the plant embryo may be cultured in the germination medium for about 20 hours. In some embodiments, the plant embryo is suspended in the germination medium and kept in constant motion. For example, vessels containing plant embryos and the germination medium may be agitated on a shaker, at a rate of between about 70 and about 120 r.p.m, as described in EXAMPLES 2 and 3. Any other methods of culturing embryos in a liquid medium are suitable in the practice of the methods of the invention.

The second step of the methods of the invention comprises assembling the cultured plant embryo into a manufactured seed. A manufactured seed typically comprises a manufactured seed coat, a nutritive medium, and a shoot restraint. A "manufactured seed coat" refers to a structure analogous to a natural seed coat that protects the plant embryo and other internal structures of the manufactured seed from mechanical damage, desiccation, from attack by microbes, fungi, insects, nematodes, birds, and other pathogens, herbivores, and pests, among other functions.

The manufactured seed coat may be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed coat is made are generally non-toxic and provide a degree of rigidity. The seed coat can be biodegradable, although typically the seed coat remains intact and resistant to penetration by plant pathogens until after emergence of the germinating embryo.

The manufactured seed coat can include a "shell" that has an opening or orifice that is covered or otherwise occluded by a lid and that contains a plant embryo. Alternatively, in place of an orifice, the shell can include a region that is thin or weakened relative to other regions of the shell. The covered orifice or thinner or weakened portion has a lower burst strength than the rest of the shell. Thus, a germinating embryo generally emerges from the manufactured seed coat by penetrating through the opening or thinner or weaker portion of the shell. The shell is generally sufficiently rigid to provide mechanical protection to the embryo, for example, during sowing, and is substantially impermeable to gases, water, and soil microbes. Typically, the radicle end of the embryo is oriented toward the opening or weaker area of the shell to facilitate protrusive growth of the primary root of the germinating embryo from the manufactured seed.

The seed coat may lack an opening or weakened or thin section, as long as it does not prevent the embryo germinating from within from growing out of the manufactured seed without fatal or debilitating injury to the tissue. To this end, polymeric materials having a high dry strength and low wet strength can be used. The seed coat can also be so constructed that it forms a self-breaking capsule (e.g., a capsule that is melted by depolymerization) or that it breaks apart easily upon application of an outwardly protrusive force from inside the manufactured seed but is relatively resistant to compressive forces applied to the outside of the seed coat (see, e.g., Japanese Patent Application No. JP 59102308; Redenbaugh (1993) In: Redenbaugh (ed.), Synseeds: Application of Synthetic Seeds to Crop Improvement, Chapter 1, CRC Press, Boca Raton, Fla.).

The manufactured seed coat may have two or more layers, each having the same or a different composition. For example, the innermost layer may include a relatively compliant and water-impermeable cellulosic material and the outer layer can comprise a polymeric material having a high dry strength and a low wet strength. Alternatively, the inner layer may include a rigid shape such as an open-ended cylinder, where at least a portion of the open end(s) is covered with an outer-layer material having a high dry strength and a low wet strength.

The manufactured seed coat may comprise a relatively compliant cellulosic or analogous material, shaped to at least partially conform to the shape of the nutritive medium and/or shoot restraint to be disposed therein. The manufactured seed coat may have at least one tapered end terminating with an orifice, which may be covered with a lid.

Additives such as antibiotics, and plant-growth regulators may be added to the manufactured seed coat, for example, by incorporation into the material forming one or more of the layers of the seed coat or by coating or otherwise treating the layer(s) with the additive by conventional means.

As used herein, a "nutritive medium" refers to a source of nutrients, such as vitamins, minerals, carbon and energy sources, and other beneficial compounds used by the embryo during germination. Thus, the nutritive medium is analogous to the gametophyte of a natural seed. A nutritive medium according to the invention may include a substance that causes the medium to be a semisolid or have a congealed consistency under normal environmental condition. Typically, the nutritive medium is in the form of a hydrated gel. A "gel" is a substance that is prepared as a colloidal solution and that will, or can be caused to, form a semisolid material. Such conversion of a liquid gel solution into a semisolid material is termed herein "curing" or "setting" of the gel. A "hydrated gel" refers to a water-containing gel. Such gels are prepared by first dissolving in water (where water serves as the solvent, or "continuous phase") a hydrophilic polymeric substance (serving as the solute, or "disperse phase") that, upon curing, combines with the continuous phase to form the semisolid material. Thus, the water becomes homogeneously associated with the solute molecules without experiencing any substantial separation of the continuous phase from the disperse phase. However, water molecules can be freely withdrawn from a cured hydrated gel, such as by evaporation or imbibition by a germinating embryo. When cured, these gels have the characteristic of compliant solids, like a mass of gelatin, where the compliance becomes progressively less and the gel becomes more "solid" to the touch as the relative amount of water in the gel is decreased.

In addition to being water-soluble, suitable gel solutes are neither cytotoxic nor substantially phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting other process.

Candidate gel solutes include, but are not limited to, the following: sodium alginate, agar, agarose, amylose, pectin, dextran, gelatin, starch, amylopectin, modified celluloses such as methylcellulose and hydroxyethylcellulose, and polyacrylamide. Other hydrophilic gel solutes can also be used, so long as they possess similar hydration and gelation properties and lack of toxicity.

Gels are typically prepared by dissolving a gel solute, usually in fine particulate form, in water to form a gel solution. Depending upon the particular gel solute, heating is usually necessary, sometimes to boiling, before the gel solute will dissolve. Subsequent cooling will cause many gel solutions to reversibly "set" or "cure" (become gelled). Examples include gelatin, agar, and agarose. Such gel solutes are termed "reversible" because reheating cured gel will re-form the gel solution. Solutions of other gel solutes require a "complexing" agent which serves to chemically cure the gel by crosslinking gel solute molecules. For example, sodium alginate is cured by adding calcium nitrate ($Ca(NO_3)_2$) or salts of other divalent ions such as, but not limited to, calcium, barium, lead, copper, strontium, cadmium, zinc, nickel, cobalt, magnesium, and iron to the gel solution. Many of the gel solutes requiring complexing agents become irreversibly cured, where reheating will not re-establish the gel solution.

The concentration of gel solute required to prepare a satisfactory gel according to the present invention varies depending upon the particular gel solute. For example, a useful concentration of sodium alginate is within a range of about 0.5% w/v to about 2.5% w/v, preferably about 0.9% w/v to 1.5% w/v. A useful concentration of agar is within a range of about 0.8% w/v to about 2.5% w/v, preferably about 1.8% w/v. Gel concentrations up to about 24% w/v have been successfully employed for other gels. In general, gels cured by complexing require less gel solute to form a satisfactory gel than "reversible" gels.

The nutritive medium typically comprises one or more carbon sources, vitamins, and minerals. Suitable carbon sources include, but are not limited to, monosaccharides, disaccharides, and/or starches. The nutritive medium may also comprise amino acids, an adsorbent composition, and a smoke suspension. Suitable amino acids, adsorbent compositions, and smoke suspensions are as described above for the germination medium. A nutritive medium may also include one or more compounds involved in nitrogen metabolism, such as urea or polyamines.

The nutritive medium may include oxygen-carrying substances to enhance both the absorption of oxygen and the retention of oxygen by the nutritive medium, thereby allowing the medium to maintain a concentration of oxygen that is higher than would otherwise be present in the medium solely from the absorption of oxygen from the atmosphere. Exemplary oxygen-carrying substances are described in U.S. Pat. No. 5,564,224, herein incorporated by reference. The nutritive medium may also contain hormones, such as abscisic acid, cytokinins, auxins, and gibberellins. Suitable hormones for use in the nutritive medium are as described above for the germination medium.

Exemplary nutritive media are described in U.S. Pat. No. 5,687,504 and in U.S. application Ser. No. 10/371,612, herein incorporated by reference. A representative nutritive medium is NM1, the composition of which is set forth in Table 1 below.

As used herein, a "shoot restraint" refers to a porous structure within a manufactured seed with an interior surface for contacting and surrounding at least the shoot end of a plant embryo and that resists penetration by the shoot end during germination. The shoot restraint prevents the shoot end of the embryo, such as the cotyledons, from growing into and becoming entrapped in the nutritive medium. The shoot restraint is porous to allow access of the embryo to water, nutrients, and oxygen. The shoot restraint may be fabricated from any suitable material, including, but not limited to, glassy, metal, elastomeric, ceramic, clay, plaster, cement, starchy, putty-like, synthetic polymeric, natural polymeric, and adhesive materials. Exemplary shoot restraints are described in U.S. Pat. No. 5,687,504, herein incorporated by reference.

In some embodiments, the methods comprise the steps of: (a) culturing plant tissue in an initiation medium to form embryogenic cells; (b) culturing the embryogenic cells of step (a) in a maintenance media to form multiplied embryogenic cells; (c) culturing the multiplied embryogenic cells of step (b) in a development medium to form somatic embryos; (d) culturing the somatic embryos of step (c) under conditions that promote embryo maturity to form post-development somatic embryos; (e) culturing the post-development somatic embryos of step (d) in a germination medium to form cultured post-development somatic embryos; and (f) assembling the cultured post-development somatic embryos of step (e) into manufactured seeds.

Steps (a) to (d) may be performed according to methods that are standard in the art and that have been previously described (see, e.g., U.S. Pat. Nos. 4,957,866; 5,034,326; 5,036,007; 5,041,382; 5,236,841; 5,294,549; 5,482,857; 5,563,061; and 5,821,126). Steps (e) and (f) are performed as described above and in EXAMPLES 1-3.

All or only part of the plant embryo may be inserted into the shoot restraint. Typically, at least the shoot end of the plant embryo is inserted into the shoot restraint. The shoot restraint may be inserted into the seed coat comprising the nutritive medium before or after inserting the plant embryo into the shoot restraint. In some embodiments, the shoot restraint is inserted into the seed coat before the embryo is placed into the restraint, as described in EXAMPLES 2 and 3. An exemplary method for assembling a plant embryo into a manufactured is described in EXAMPLE 1.

The manufactured seeds may be incubated under conditions suitable for germination of plant embryos. Conditions suitable for germination of manufactured seeds are standard in the art, and include conditions suitable for germination of natural seeds. For example, the manufactured seeds may be sown in any of a variety of environments, such as in sand, vermiculite, sterile soil, and/or in the field (natural soil). For example, sterile Coles™ washed sand, which is available from a variety of gardening supply stores, may be used. Exemplary conditions suitable for germination of the plant embryo in manufactured seeds are described in EXAMPLE 1.

The methods of the invention improve the germination of manufactured seeds. For example, culturing the plant somatic embryo in a germination medium increased the percentage of normal germinants compared to an otherwise identical method in which the plant somatic embryo was not cultured in a germination medium, as shown in EXAMPLES 2 and 3. For example, normalcy, epicotyl presence, and radicle length for somatic embryos cultured in a liquid germination medium before assembly into manufactured seed were significantly greater than for embryos that were directly assembled into manufactured seed. In some embodiments of the methods of the invention, culturing the plant somatic embryo in germination medium improved germination by at least about 17%, as shown in EXAMPLE 2.

The term "normal germinant" or "normalcy" denotes the presence of all expected parts of a plant at time of evaluation. The expected parts of a plant may include a radicle, a hypocotyl, one or more cotyledon(s), and an epicotyl. The term "radicle" refers to the part of a plant embryo that develops into the primary root of the resulting plant. The term "cotyledon" refers generally to the first, first pair, or first whorl (depending on the plant type) of leaf-like structures on the plant embryo that function primarily to make food compounds in the seed available to the developing embryo, but in some cases act as food storage or photosynthetic structures. The term "hypocotyl" refers to the portion of a plant embryo or seedling located below the cotyledons but above the radicle. The term "epicotyl" refers to the portion of the seedling stem that is above the cotyledons. In the case of gymnosperms, normalcy is characterized by the radicle having a length greater than 3 mm and no visibly discernable malformations compared to the appearance of embryos germinated from natural seed. It is important to note that, as long as all parts of an embryo have germinated, the corresponding germinant probably has the potential to become a normal seedling. There is no reason to believe that any malformations observed in EXAMPLES 2 and 3 below are fatal to germinants. Noting the quantity and quality of malformation is a convenient way to comparatively evaluate the various methods and means employed for making manufactured seeds. Fortunately, plant embryonic tissue is exquisitely sensitive to non-natural conditions and manifests that sensitivity in ways discernable to a trained observer.

The following examples merely illustrate the best mode now contemplated for practicing the invention, but should not be construed to limit the invention.

EXAMPLE 1

This Example shows a general method for assembling plant embryos into manufactured seeds and germinating manufactured seeds.

Representative methods used for making manufactured seeds are described in U.S. Pat. Nos. 6,119,395, 5,701,699, and 5,427,593, incorporated herein by reference. Seed coats were made by plunging paper straw segments into a molten wax formulation. The segments were removed, excess wax drained and the remaining wax allowed to solidify. Ceramic shoot restraints were made by injecting a porcelain slip into a preformed mold with a pin in the center to create the shoot accepting cavity. The slip was allowed to dry to a consistency that allowed removal of the preformed restraint. The restraint was subsequently heated to a temperature that allows the porcelain to form a porous, but fused structure. The restraint was then acid washed to remove impurities. Lids were made by pre-stretching Parafilm™ (Pechiney Plastic Packaging, Chicago, Ill. 60631).

The nutritive medium NM1 (see Table 1) was prepared from pre-made stocks. The required amount of each stock solution (that is not heat-labile) was added to water. Non-stock chemicals (such as charcoal, and agar) were weighed out and added directly to the solution. After all the non-heat-labile chemicals and compounds were added, the medium was brought up to an appropriate volume and the pH was adjusted. The medium was then sterilized by autoclaving. Filter-sterilized heat-labile components (such as sucrose, vitamins, and amino acids) were added after the medium had cooled.

Manufactured seed were assembled by placing a cotyledon restraint on a flat "puck". A pre-made seedcoat was then placed over the restraint and the unit dipped in molten wax to seal the two units together. The wax was then allowed to solidify and the resulting seedcoat was filled with nutritive medium via a positive displacement pump. The nutritive media was then allowed to solidify and the seed was removed from the flat "puck". The open end (non-embryo containing end) was then sealed by dipping in molten wax. After the plant embryos were inserted into the shoot restraints, as described in EXAMPLES 2 and 3, the seeds were sealed by laying lids over the open end of the manufactured seed and fusing the lids to the surface with heat. The manufactured seeds were then swabbed with anti-microbial agents.

A suitable amount of sterile sand was prepared by baking 2 liters of sand at a temperature of 375° F. for 24 hours. The sand was then added to pre-sterilized trays and 285 ml water was added. Furrows were then formed and the box was sealed. The box containing the sand was then autoclaved for 1 hour at 121° C. and 1 atmospheric pressure.

The manufactured seeds were sown in the sand and allowed to germinate. Typically, the manufactured seeds were cultured under continuous light at room temperature (23° C.) for four to five weeks.

TABLE 1

Composition of Media for Manufactured Seeds

| Constituent | NM1 (mg/l) | NM2 (mg/l) |
|---|---|---|
| $NH_4NO_3$ | 301.1 | 206.25 |
| $(NH_4)_2MoO_4$ | 0.06 | |
| $KNO_3$ | | 1170 |
| $MgSO_4.7H_2O$ | 1000 | 185 |
| $KH_2PO_4$ | 1800 | 85 |
| $CaCl_2.2H_2O$ | 299.2 | 220 |
| KI | | 0.415 |
| $H_3BO_3$ | 10.0 | 3.1 |
| $MnSO_4.H_2O$ | | 8.45 |
| $MnCl_2.4H_2O$ | 6.0 | |
| $ZnSO_4.7H_2O$ | 0.8 | 4.3 |
| $Na_2MoO_4.2H_2O$ | | 0.125 |
| $CuSO_4.5H_2O$ | | 0.0125 |
| $CuCl_2.2H_2O$ | 0.5 | |
| $CoCl_2.6H_2O$ | | 0.0125 |
| $FeSO_4.7H_2O$ | | 13.925 |
| Ferric citrate | 60 | |
| $Na_2EDTA$ | | 18.625 |
| Nicotinic acid | 1 | 0.5 |
| Pyridoxine.HCl | 0.25 | 0.5 |
| Thiamine.HCl | 1 | 1 |
| Glycine | | 2 |
| Myo-Inositol | 100 | 100 |
| Riboflavin | 0.125 | |
| Ca-pantothenate | 0.5 | |
| Biotin | 0.001 | |
| Folic Acid | 0.125 | |
| L-asparagine | 106.7 | |
| L-glutamine | 266.7 | |
| L-lysine.2H$_2$O | 53.3 | |
| DL-serine | 80 | |
| L-proline | 53.3 | |
| L-arginine.HCl | 2266.7 | |
| L-valine | 53.3 | |
| L-alanine | 53.3 | |
| L-leucine | 80 | |
| L-threonine | 26.7 | |
| L-phenylalanine | 53.3 | |
| L-histidine | 26.7 | |
| L-tryptophan | 26.7 | |
| L-isoleucine | 26.7 | |
| L-methionine | 26.7 | |
| L-glycine | 53.3 | |
| L-tyrosine | 53.3 | |
| L-cysteine | 26.7 | |
| Urea | 800 | |
| Sucrose | 50 | 50 |
| Agar | 18 | 18 |
| Charcoal | 2.5 | 2.5 | pH adjusted to 5.7

EXAMPLE 2

This Example shows a representative method of the invention for improving the germination of manufactured seeds containing Douglas-fir zygotic and somatic embryos.

At the end of the maturation process, somatic embryos do not have as high levels of storage products as zygotic embryos do. This may be a reason why somatic embryos do not germinate as vigorously as zygotic embryos when placed into manufactured seeds. Nutrient loading of somatic embryos by culturing them in a germination medium may improve the germination efficiency of manufactured seeds containing somatic embryos.

Methods: Douglas-fir seeds were surface-sterilized by methods similar to those previously described (Cyr et al. (1991) *Seed Sci. Res.* 1:91-97). Zygotic embryos were dissected by first cracking open the seedcoat to remove it, then removing undamaged embryo from the megagametophyte with scalpel and forceps in a laminar flow hood. Douglas-fir somatic embryos were obtained as previously described (see, e.g., U.S. Pat. Nos. 5,036,007; 5,041,382; 5,236,841; 5,294,549; 5,482,857; 5,563,061 and 5,821,126). Manufactured seeds were assembled as described in EXAMPLE 1. Zygotic and cold-treated somatic embryos were subjected to the following treatments:

1. Zygotic embryos were directly inserted into the shoot restraints of manufactured seeds;
2. Somatic embryos were directly inserted into the shoot restraints of manufactured seed;
3. Zygotic embryos were transferred into germination medium NM1 without agar (Table 1) in a flask using fine forceps. The flask was set on a rotary shaker at 90 r.p.m. for 20 hours in the dark, after which embryos and charcoal were collected on a Whatman # 1 filter paper. The filter papers were placed on medium NM2 (Table 1) before inserting the embryos into shoot restraints;

4. Somatic embryos were transferred into germination medium NM1 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints;

5. Zygotic embryos were transferred into germination medium NM2 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints;

6. Somatic embryos were transferred into germination medium NM2 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints;

7. Somatic embryos were placed on medium NM2 before inserting the embryos into shoot restraints;

8. Zygotic embryos were transferred into germination medium NM1 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints;

9. Somatic embryos were transferred into germination medium NM1 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints;

10. Zygotic embryos were transferred into germination medium NM2 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints; and 11. Somatic embryos were transferred into germination medium NM2 without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 before inserting the embryos into shoot restraints.

For treatments 7-11, embryos were not assembled into manufactured seeds. There were 6 replicates for each treatment and 5 seeds were used for each replicate. The manufactured seeds were sealed and germinated as described in EXAMPLE 1. Germination was evaluated at 41 days past sowing.

Results: The percentages of germinants as assessed at day 41 after sowing are shown in Table 2.

TABLE 2

Percentages of Germinants

| Treatment | Full Germination $\alpha < 0.0001$[1] |
|---|---|
| 1 | 93.3%[A] |
| 2 | 30.0%[B] |
| 3 | 90.0%[A] |
| 4 | 56.7%[B] |
| 5 | 93.3%[A] |
| 6 | 53.3%[B] |

[1]Means followed by the same letter not significantly different.

Table 3 shows the percentages of germinants in each normalcy category. Normalcy refers to the presence of all expected parts of a plant (i.e., radicle, hypocotyl, cotyledon(s), epicotyl) at time of evaluation. A normal germinant was defined as having a radicle with a length greater than 3 mm and no visibly discernable malformations compared to the appearance of (1) in the case of manufactured seeds, embryos germinated from natural seed, and, or (2) in the case of bare embryos, control (non-treated) bare embryos grown on the surface of nutrient agar or the like.

TABLE 3

Percentages of Normal Germinants

| Treatment | Normal $\alpha < 0.0001$[1] |
|---|---|
| 1 | 100.0%[A] |
| 2 | 26.7%[C] |
| 3 | 90.0%[A] |
| 4 | 63.3%[B] |
| 5 | 93.3%[A] |
| 6 | 53.3%[B] |

[1]Means followed by the same letter not significantly different.

Table 4 shows the percent normalcy for treatments 7-11, in which embryos were not placed into manufactured seeds.

TABLE 4

Normalcy for Bare Embryo Germination

| Treatment | Normalcy |
|---|---|
| 7 | 83.33% |
| 8 | 80.00% |
| 9 | 93.33% |
| 10 | 93.33% |
| 11 | 73.33% |

The results show that culturing somatic embryos in a germination medium before assembling them into manufactured seeds improves germination. Normalcy, epicotyl presence, and radicle length for somatic embryos cultured in germination media before assembly into manufactured seed were significantly greater than for embryos that were directly assembled into manufactured seed.

EXAMPLE 3

This Example shows a representative method of the invention for improving the termination of manufactured seeds containing Douglas-fir somatic embryos.

Methods: Manufactured seeds were assembled as described in EXAMPLE 1. Douglas-fir somatic embryos were obtained as described in EXAMPLE 2. After cold treatment, somatic embryos were subjected to the following treatments:

1. Cold-treated somatic embryos were placed on medium NM2 (Table 1) containing 8 g/l of agar and 20 g/l of sucrose for 20 hours before they were inserted into shoot restraints; and
2. Cold-treated somatic embryos were transferred into germination medium NM1 (Table 1) without agar in a flask using fine forceps. The flask was set on a rotary shaker at 90 r.p.m. for 20 hours in the dark, after which embryos and charcoal were collected on a Whatman # 1 filter paper. The filter papers were placed on medium NM2 containing 8 g/l of agar and 20 g/l of sucrose for ease of separating the embryos from the charcoal, after which the embryos were separated from the filter paper and charcoal and placed on a fresh plate of medium NM2 containing 8 g/l of agar and 20 g/l of sucrose before inserting the embryos into shoot restraints.

There were 6 replicates for each treatment and 10 seeds were used for each replicate. The manufactured seeds were sealed and germinated as described in EXAMPLE 1.

Results: At all time points examined after sowing, the percentage of fully germinated embryos was higher for manufactured seeds after treatment 2 than after treatment 1, as shown in Table 5.

TABLE 5

Percentages of Fully Germinated Embryos

| Days Past Sowing | Percentage of Fully Germinated Embryos | |
|---|---|---|
| | Treatment 1 | Treatment 2 |
| 10 | 0.0% | 1.6% |
| 12 | 0.0% | 6.6% |
| 14 | 0.0% | 13.3% |
| 17 | 1.6% | 25.0% |
| 19 | 6.7% | 30.0% |
| 26 | 11.7% | 33.3% |
| 28 | 16.7% | 33.3% |
| 31 | 16.7% | 33.3% |
| 35 | 20.0% | 33.0% |
| 39 | 21.7% | 33.3% |
| 42 | 25.0% | 35.0% |
| 45 | 25.0% | 35.0% |
| 47 | 25.0% | 35.0% |
| 55 | 25.0% | 35.0% |

The percentage of manufactured seeds that had fully germinated at 55 days past sowing was higher after treatment 2 (35%) than after treatment 1 (25%). The normalcy of the germinants was also assessed. Normalcy refers to the presence of all expected parts of a plant (i.e., radicle, hypocotyl, cotyledon(s), epicotyl) at time of evaluation. A normal germinant was defined as having a radicle with a length greater than 3 mm and no visibly discernable malformations compared to the appearance of an embryo germinated from natural seed. The percentage of normal germinants was 21.7% after treatment 1 and 38.3% after treatment 2. The mean radicle lengths of the germinants were significantly different after the two treatments ($a=0.0001$). The mean radicle length was 0.52 cm after treatment 1 and 1.49 cm after treatment 2.

These results show that culturing somatic embryos in germination medium (treatment 2) improves the germination of manufactured seeds containing these somatic embryos compared to manufactured seeds containing untreated somatic embryos (treatment 1), probably by increasing nutrient availability. For example, culturing the somatic embryos in germination medium increased normalcy by about 17% compared to controls. Culturing somatic embryos in germination medium and encasing cotyledons in hydrated gel also significantly improved root lengths.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for improving germination of a manufactured seed, comprising:
    (a) culturing a post-development plant embryo in a germination medium comprising amino acids to form a cultured post-development plant embryo; and
    (b) assembling the cultured post-development plant embryo into a manufactured seed.

2. The method of claim 1, wherein the plant embryo is cultured in the germination medium for between about 4 hours and about 24 hours.

3. The method of claim 2, wherein the plant embryo is cultured in the germination medium for about 20 hours.

4. The method of claim 1, wherein the germination medium comprises a carbon source, wherein the carbon source is at least one of sucrose, glucose, maltose, fructose, and starch.

5. The method of claim 4, wherein the carbon source is sucrose.

6. The method of claim 1, wherein the germination medium comprises an adsorbent composition.

7. The method of claim 6, wherein the adsorbent composition is charcoal.

8. The method of claim 1, wherein the germination medium comprises a polyamine.

9. The method of claim 1, wherein the germination medium comprises at least one hormone.

10. The method of claim 9, wherein the hormone comprises at least one gibberellin.

11. The method of claim 1, wherein the germination medium comprises at least 8 components selected from the group consisting of: charcoal, a carbon source, urea, $KNO_3$, $NH_4NO_3$, $CuCl_2$, $CuSO_4$, KI, $KH_2PO_4$, $CaCl_2$, $MgSO_4$, $Na_2EDTA$, $FeSO_4$, ferric citrate, $MnSO_4$, $MnCl_2$, $H_3BO_3$, $ZnSO_4$, $CoCl_2$, $Na_2MoO_4$, $(NH_4)_2MoO_4$, thiamine, riboflavin, pyridoxine, HCl, Ca-pantothenate, nicotinic acid, biotin, folic acid, and myo-inositol.

12. The method of claim 11, wherein the germination medium further comprises at least one component selected from the group consisting of: polyamines, oxygen-carrying compounds, and a smoke suspension.

13. The method of claim 1, wherein the plant embryo is a post-development somatic plant embryo.

14. The method of claim 13, wherein the somatic plant embryo is a conifer somatic plant embryo.

15. The method of claim 14, wherein the somatic plant embryo is a Douglas-fir somatic plant embryo.

16. The method of claim 14, wherein the somatic plant embryo is a loblolly pine somatic plant embryo.

17. The method of claim 1, wherein the plant embryo is a post- development somatic plant embryo produced by a method comprising:
  (a) culturing plant tissue in an initiation medium to form embryogenic cells;
  (b) culturing the embryogenic cells of step (a) in a maintenance media to form multiplied embryogenic cells;
  (c) culturing the multiplied embryogenic cells of step (b) in a development medium to form somatic plant embryos; and
  (d) culturing the somatic plant embryos of step (c) under conditions that promote embryo maturity to form post-development somatic plant embryos.

* * * * *